United States Patent
O'Brien et al.

(10) Patent No.: US 7,702,398 B2
(45) Date of Patent: *Apr. 20, 2010

(54) CONNECTION FOR A COILED LEAD TO AN ELECTRICAL CONTACT FOR AN IMPLANTABLE MEDICAL DEVICE

(75) Inventors: Robert C. O'Brien, Miramar, FL (US); Robert Naugler, Eldersburg, MD (US); Warren Dabney, Orchard Park, NY (US); Christine A Frysz, Orchard Park, NY (US); Andrew Fisk, Baltimore, MD (US)

(73) Assignee: Greatbatch Ltd., Clarence, NY (US)

( * ) Notice: Subject to any disclaimer, the term of this patent is extended or adjusted under 35 U.S.C. 154(b) by 109 days.

This patent is subject to a terminal disclaimer.

(21) Appl. No.: 11/682,398

(22) Filed: Mar. 6, 2007

(65) Prior Publication Data

US 2007/0173115 A1 Jul. 26, 2007

Related U.S. Application Data

(62) Division of application No. 10/968,310, filed on Oct. 19, 2004, now Pat. No. 7,383,090.

(60) Provisional application No. 60/512,739, filed on Oct. 20, 2003.

(51) Int. Cl.
*A61N 1/04* (2006.01)

(52) U.S. Cl. ............................ 607/116; 607/36; 607/37; 607/38; 607/117; 607/119; 600/373; 600/382

(58) Field of Classification Search ............. 607/36–37, 607/116–117, 119–120; 600/373–391
See application file for complete search history.

(56) References Cited

U.S. PATENT DOCUMENTS

| | | | |
|---|---|---|---|
| 4,437,474 A * | 3/1984 | Peers-Trevarton | 607/119 |
| 4,735,208 A | 4/1988 | Wyler et al. | |
| 5,902,236 A | 5/1999 | Iversen | |
| 6,024,702 A | 2/2000 | Iversen | |
| 6,192,279 B1 * | 2/2001 | Barreras et al. | 607/117 |
| 6,236,892 B1 | 5/2001 | Feler | |
| 6,249,709 B1 | 6/2001 | Conger et al. | |
| 6,366,820 B1 | 4/2002 | Doan et al. | |
| 6,597,954 B1 | 7/2003 | Pless et al. | |
| 6,606,521 B2 | 8/2003 | Paspa et al. | |
| 6,662,035 B2 | 12/2003 | Sochor | |
| 2002/0052636 A1 | 5/2002 | Bardy et al. | |
| 2002/0099430 A1 | 7/2002 | Verness | |
| 2003/0036788 A1 * | 2/2003 | Coe et al. | 607/119 |
| 2003/0212395 A1 | 11/2003 | Woloszko et al. | |
| 2004/0024440 A1 | 2/2004 | Cole | |
| 2005/0027341 A1 * | 2/2005 | Schrom et al. | 607/116 |

* cited by examiner

*Primary Examiner*—Carl H Layno
*Assistant Examiner*—Deborah Malamud
(74) *Attorney, Agent, or Firm*—Michael F. Scalise

(57) ABSTRACT

High reliability electrical connections between a helical strand and flat electrodes, such as strip electrodes found in implantable neurostimulator system, are described. The connection consists of a crimp joint in which an inside diameter mandrel is used to provide the coil with sufficient radial rigidity to ensure structural integrity of the crimp. The mandrel is made of a relatively soft biocompatible material that deforms rather than damages the fine wires of the helical strand during crimping. The crimp is accomplished by radial deformation of an annular or semi-annular crimping member that receives the helical strand/mandrel assembly.

21 Claims, 11 Drawing Sheets

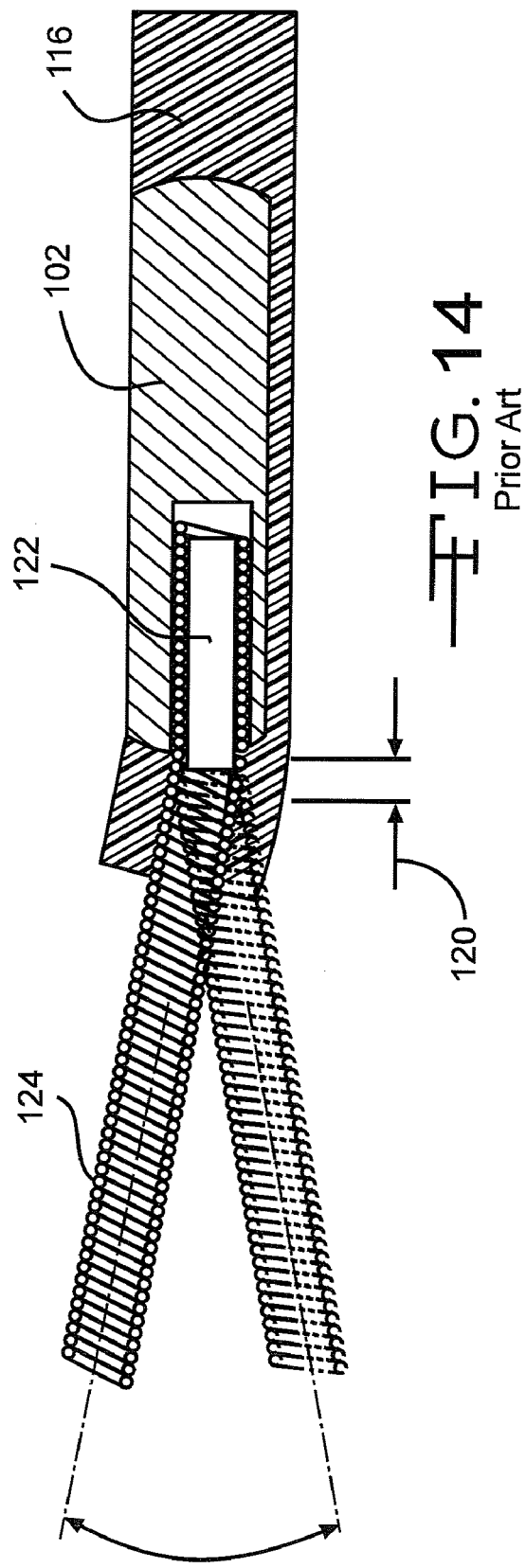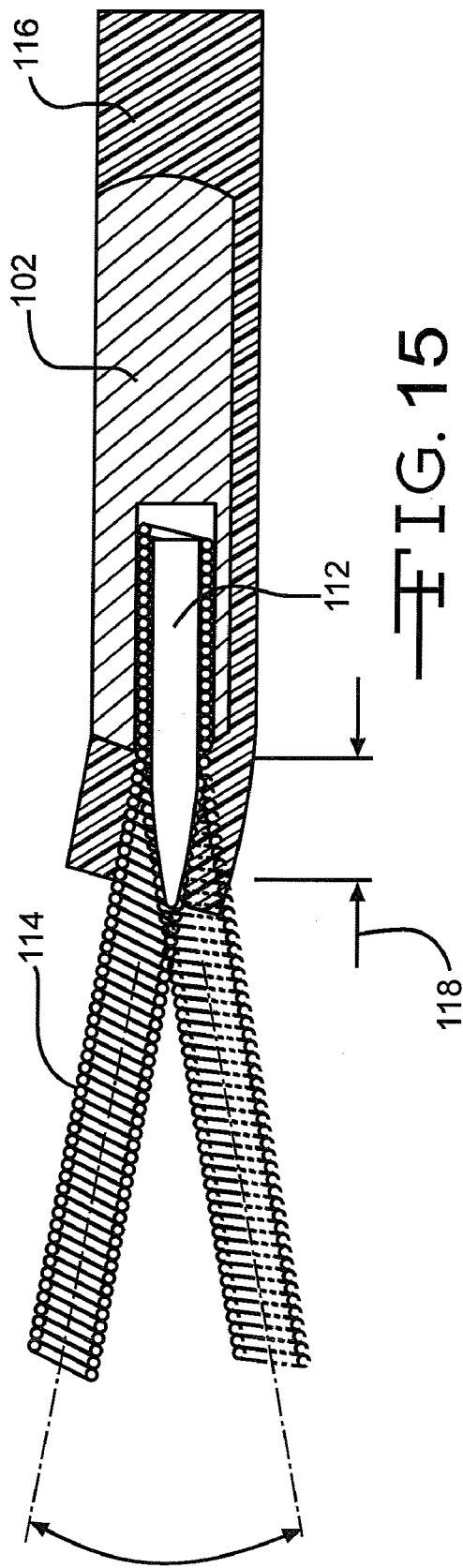

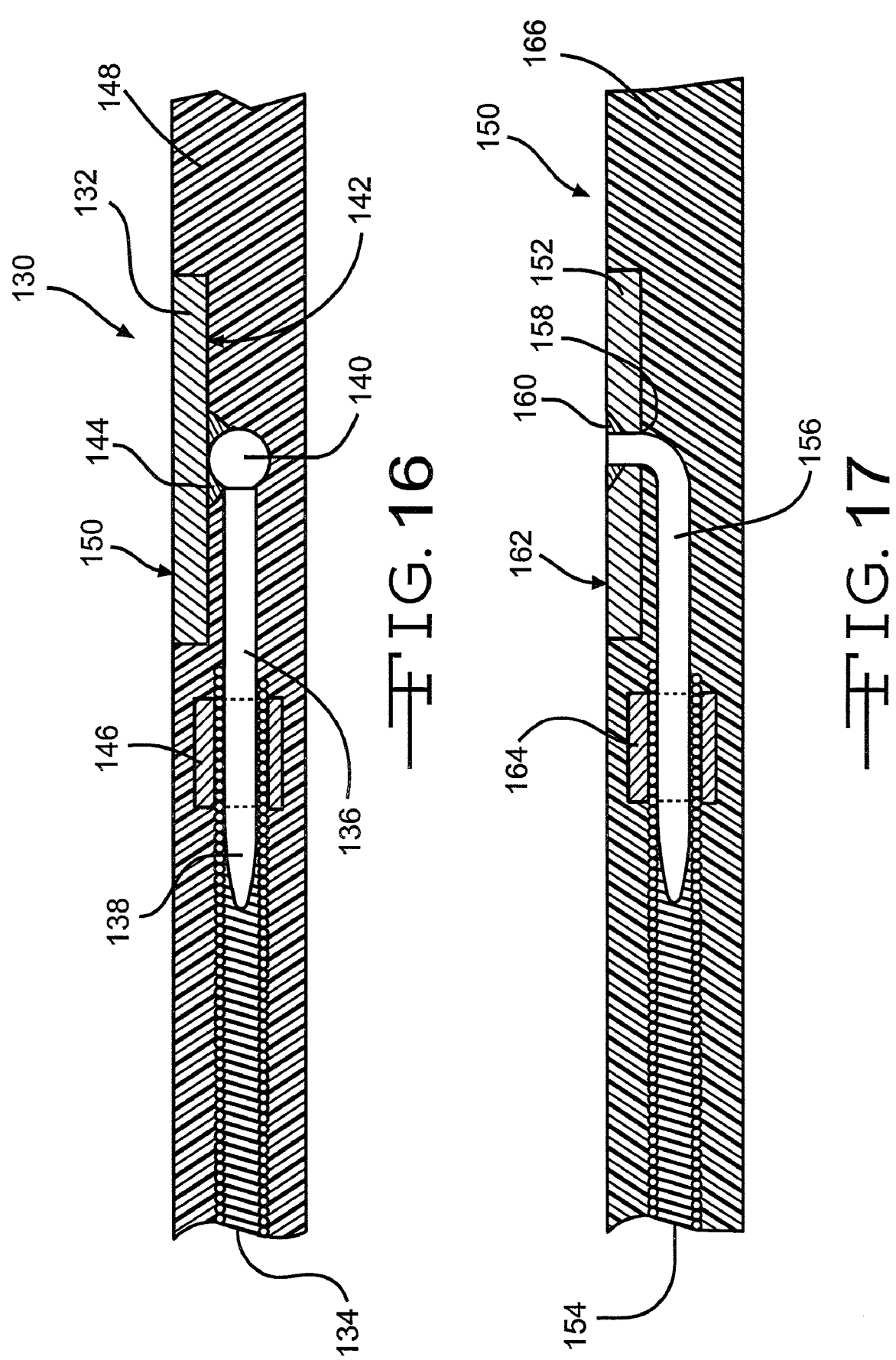

CONNECTION FOR A COILED LEAD TO AN ELECTRICAL CONTACT FOR AN IMPLANTABLE MEDICAL DEVICE

CROSS-REFERENCE TO RELATED APPLICATIONS

This application is a divisional of U.S. application Ser. No. 10/968,310, filed Oct. 19, 2004, now U.S. Pat. No. 7,383,090, which claims priority from provisional application Ser. No. 60/512,739, filed Oct. 20, 2003.

BACKGROUND OF THE INVENTION

This invention relates to high reliability electrical attachments between coiled leads and flat electrodes, such as strip electrodes found in implantable neurostimulator systems. The requirements for the attachment are biocompatibility, isolation from body fluids, and long-term mechanical/electrical continuity under cyclic stress.

A typical strip electrode consists of a thin, flat electrical contact of biocompatible, conductive material. A typical lead consists of a tightly wound coil of one or more helical strands of fine, fatigue resistant wire or filar elements. After attachment of the helical strand to the electrical contact, the entire assembly is potted or embedded in a flat sheet of elastomer so that only the face of the contact is exposed to body fluids.

Implantable leads are made of wires typically about 0.002 inches to 0.004 inches in diameter. These wires are formed into coils or helical strands about 0.015-inches in diameter. Leads are coiled so they can withstand constant flexing and bending forces as a result of body movement. Because of the very fine wire diameters, however, the resulting helical strands are difficult to attach to electrical contacts by laser welding. Crimping is the preferred attachment method. In that respect, the present invention is directed to ensuring that the crimped connection between a helical strand and an electrical contact maintains the same degree of reliability as is built into the coiled lead itself.

SUMMARY OF THE INVENTION

The connection between a coiled lead or helical strand and an electrical contact consists of a crimp joint in which an inside diameter mandrel is used to provide the coil with sufficient radial rigidity to ensure structural integrity of the crimp. The mandrel is made of a relatively soft biocompatible material that deforms rather than damages the fine wires of the helical strand during crimping. The crimp is accomplished by radial deformation of an annular or semi-annular crimping member that receives the helical strand/mandrel assembly.

In one embodiment, the crimping member is a porous, deformable disk having an axial hole that receives the electrical contact and a radial hole that receives the helical strand/mandrel assembly. This deformable crimping member is subjected to a cold coining process that provides a secure crimp joint to the helical strand/mandrel assembly with a portion of the crimping member being extruded into a circumferential groove or channel in the central electrical contact. In that manner, the deformed crimping member creates a secure connection to the helical strand comprising the lead as well as to the electrical contact.

In another embodiment, there is no deformable crimping member. Instead, the electrical contact made of a porous sintered material is itself deformable. That way, the electrical contact is provided with a radial bore that receives the mandrel supported in the lumen at the distal end of the helical strand. This assembly is inserted into the radial bore in the contact, which is then deformed into a locking relationship with the helical strand and mandrel.

In another embodiment, as before, the integrity of the crimp is enabled by the presence of a relatively soft mandrel positioned inside the diameter of the helical strand. The mandrel has a distal portion that is secured to the back of the electrical contact by means of a weld, braze, or solder joint. Alternatively, the distal portion of the mandrel is inserted into a through-hole in the electrical contact, secured from the top face, and then bent over until the helical strand/mandrel connection is parallel to the back face of the contact. In any event, the crimping member consists of an annular or semi-annular crimp socket surrounding the helical strand/mandrel assembly.

These and other aspects of the present invention will become more apparent to those skilled in the art by reference to the following description and to the appended drawings.

BRIEF DESCRIPTION OF THE DRAWINGS

FIG. 14 is a side elevational view, partly in cross-section, showing a connection for a helical strand 124 to the electrical contact 102 according to the prior art.

FIG. 15 is a side elevational view, partly in cross-section, showing the present invention connection of the helical strand 114 to the electrical contact 102.

FIG. 16 is a side elevational view, partly in cross-section, of another embodiment of a headed mandrel 136 crimped to a helical strand 134 secured to an electrical contact 132 and encased in an elastomeric material 148.

FIG. 17 is a side elevational view, partly in cross-section, of another embodiment of a mandrel 156 supported by a helical strand 154 secured to an electrical contact 152 and encased in a elastomeric material 166.

DETAILED DESCRIPTION OF THE PREFERRED EMBODIMENTS

Figure 1:
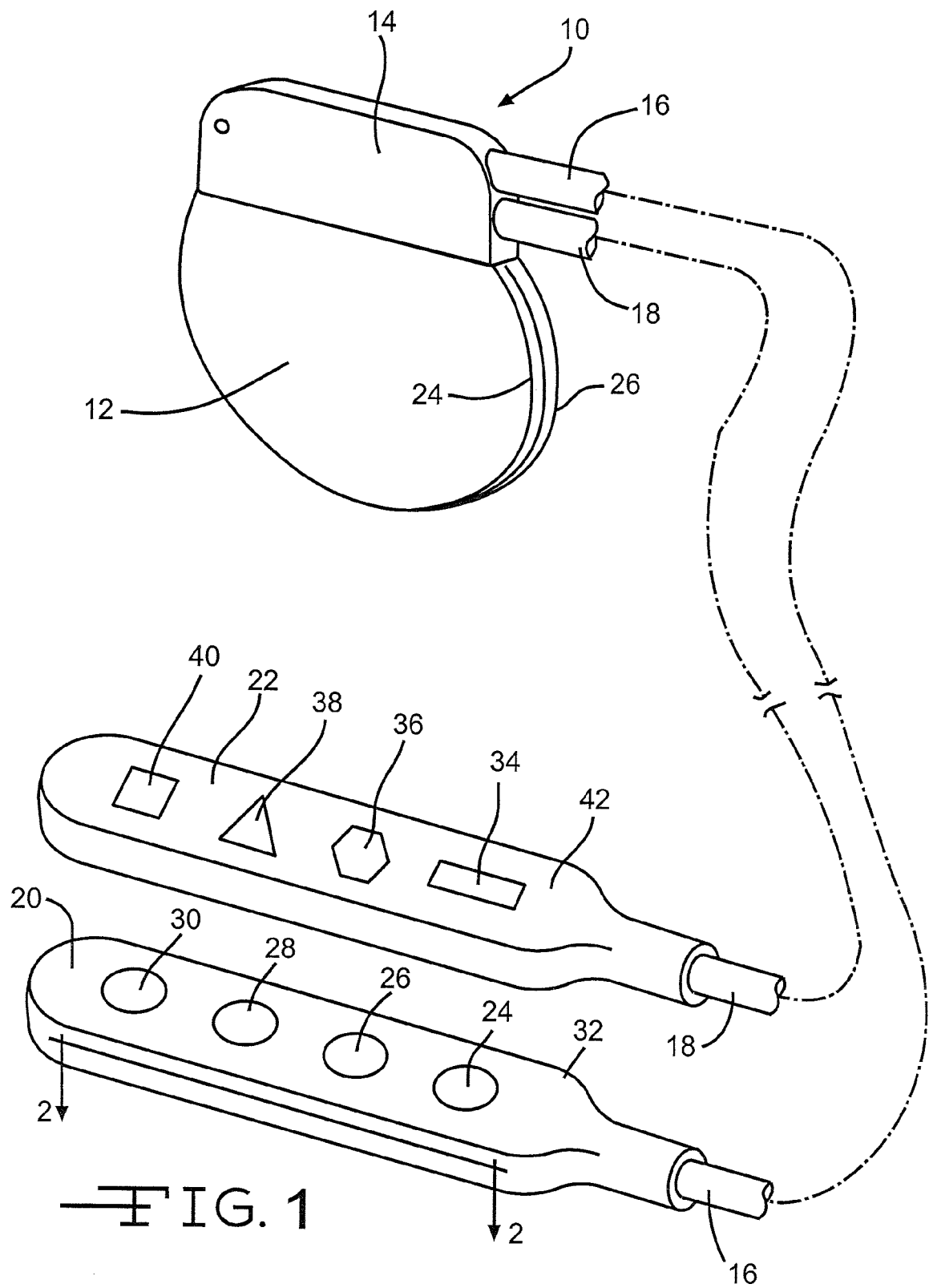
FIG. 1 is a perspective view, partly in phantom, showing an implantable medical device 10 connected to a pair of strip electrodes 20 and 22 by respective coiled leads 16 and 18.

Referring now to the drawings, FIG. 1 illustrates an implantable medical device 10 comprising a housing 12 supporting a header 14 connecting coiled leads 16 and 18 to respective strip electrodes 20 and 22. The housing 12 is of a conductive material, such as of titanium or stainless steel. Preferably, the medical device housing 12 comprises mating clamshell portions 24 and 26 in an overlapping relationship. The clamshell housing portions are hermetically sealed together, such as by laser or resistance welding, to provide an enclosure for control circuitry (not shown) connected to a power supply (not shown), such as a battery. There may also be a capacitor for a medical device such as a defibrillator. U.S. Pat. No. 6,613,474 to Frustaci et al. contains a more detailed description of a housing comprising mating clamshell portions. This patent is assigned to the assignee of the present invention and incorporated herein by reference. The housing 12 can also be of a deep drawn, prismatic and cylindrical design, as is well known to those skilled in the art.

The header 14 is mounted on the housing 12 and comprises a body of molded elastomeric material supporting terminal blocks (not shown) that provide for plugging the proximal ends of leads 16 and 18 therein to electrically connect them to the control circuitry and power supply contained inside the housing. The distal ends of the leads 16, 18 connect to the respective strip electrodes 20 and 22. For a more detailed description of the header assembly, reference is made to U.S. Pat. No. 7,167,749 to Biggs et al., which is assigned to the assignee of the present invention and incorporated herein by reference.

The strip electrodes are surgically secured to body tissue whose proper functioning is assisted by the medical device. In that respect, the implantable medical device 10 is exemplary of any one of a number of known implantable therapeutic devices such as spinal cord stimulation devices, vagus nerve stimulation devices for epilepsy, and functional electrical stimulation devices for paralysis, and the like. For example, in an implantable pulse generator for spinal cord stimulation to control pain, the circuitry provides a pulsed stimulating signal that can be current controlled or voltage controlled. The signal is delivered to nerves entering the spinal cord by means of implanted insulated coiled leads terminating at strip electrodes such as those shown in FIG. 1.

Figure 2:
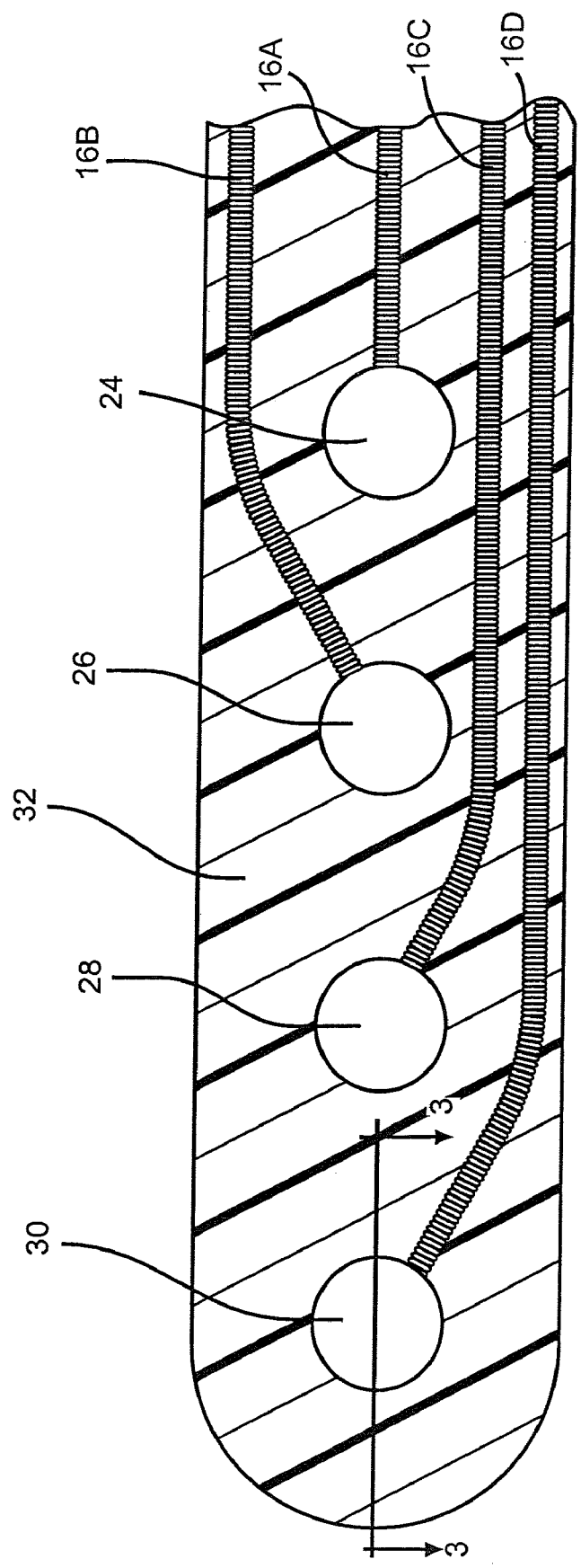
FIG. 2 is a cross-sectional view along line 2-2 of FIG. 1.

The strip electrodes 20 and 22 can be similar or different in construction. Strip electrode 20 comprises four electrical contacts 24, 26, 28 and 30, each having a circular shape in plan view and potted in an elastomeric material 32. Strip electrode 22 comprises four electrical contacts 34, 36, 38 and 40 potted in an elastomeric material 42. These contacts are square, triangular, hexagonal, and rectangular in plan view, respectively. In that respect, the present invention is not limited to the exact shape of the electrical contact and is adaptable to contacts having a myriad of shapes in plan form. Nonetheless, the present invention will be described with respect to strip electrode 20 shown in greater detail in FIG. 2 with the understanding that strip electrode 22 is generally similar in construction.

As shown, each electrical contact 24, 26, 28 and 30 is individually connected to the medical device 10 by a helical strand or filar of the coiled lead 16. Suitable materials for the electrical contacts include carbon such as pyrolytic carbon, titanium, zirconium, niobium, molybdenum, palladium, hafnium, tantalum, tungsten, iridium, platinum, gold, and alloys thereof. Stainless steel, MP35N®, ELGILOY® are other suitable alloys. The helical strands can be co-axial or they can be coiled side-by-side along the length of the coiled lead 16 until it enters the elastomeric material 42 of the strip electrode 20. There, the individual helical strands 16A, 16B, 16C and 16D separate from the bundle and connect to the individual electrical contacts 24, 26, 28 and 30, respectively. Each helical strand is formed of a conductive, fatigue resistant material such as ELGILOY® (cobalt 40%, chromium 20%, nickel 15%, molybdenum 7%, manganese 2%, carbon <0.10%, beryllium <0.10%, and iron 5.8%, by weight) or MP35N® (nickel 35%, cobalt 35%, chromium 20%, and molybdenum 10%, by weight) alloys. The coiled leads comprised of the helical strands exhibit the desired mechanical properties of low electrical resistance, high corrosion resistance, flexibility, strength and fatigue resistance required for long term duty inside a human body, and the like.

Figure 3:
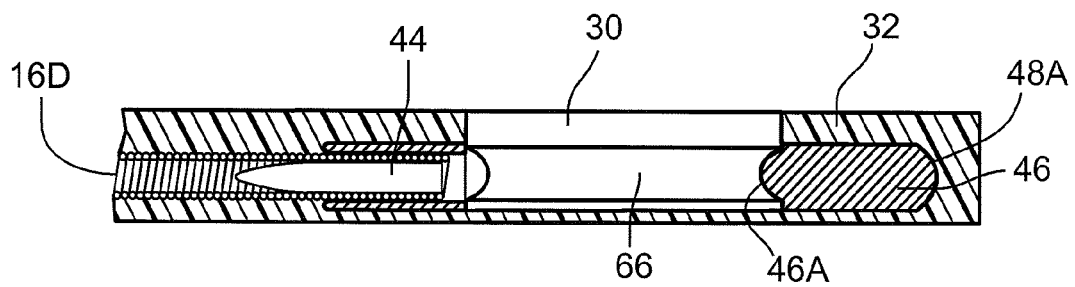
FIG. 3 is a side elevational view, partly in cross-section, showing a helical strand 16D of the coiled lead 16 crimped to an electrical contact 30 according to the present invention and encased in an elastomeric material 32.

FIG. 3 shows a cross-sectional, view of helical strand 16D secured to electrical contact 30. A deformable mandrel 44 is inserted into the distal end of the helical strand 16D. Suitable materials for the mandrel include stainless steel, titanium, zirconium, niobium, molybdenum, palladium, hafnium, tantalum, tungsten, iridium, platinum, gold, and alloys thereof. A crimping member 46 is then coined into locking contact with the helical strand 16D and the surrounded electrical contact 30. The process for coining the helical strand 16D into this locking relationship will now be described in greater detail in the progression of FIGS. 4 to 8.

Figure 4:
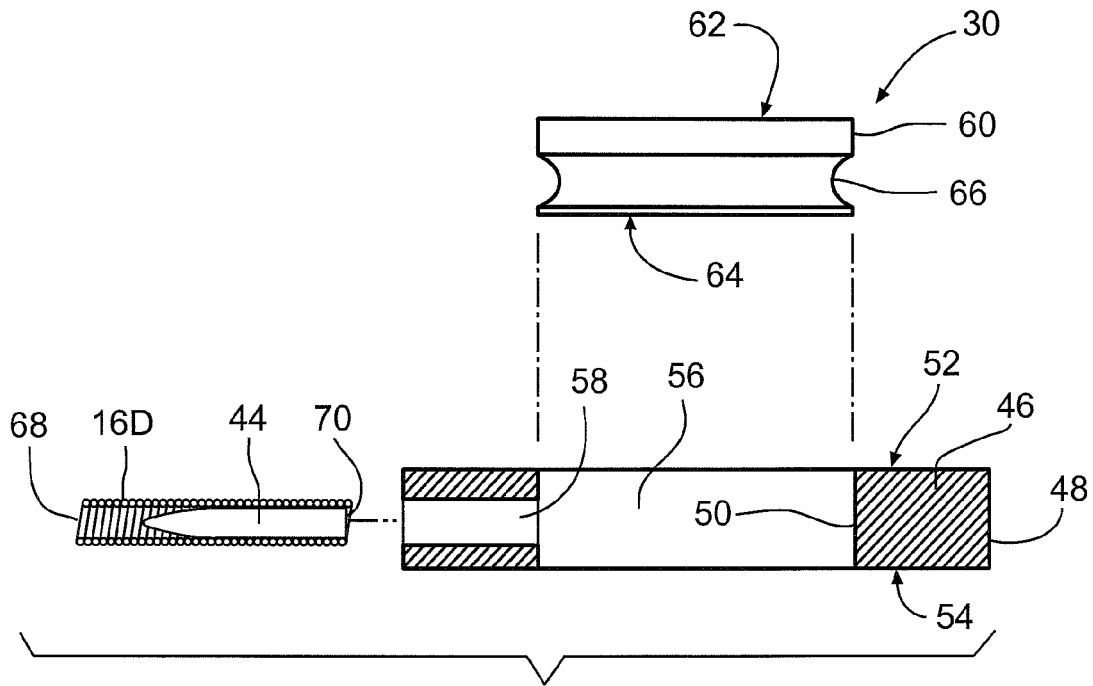
FIG. 4 is a side elevational view, partly in cross-section, showing the electrical contact 30 prior to being moved into the central opening 56 in a deformable crimping member 46 and the helical strand 16D/mandrel 44 prior to being moved into an axial bore 58 in the crimping member.

As shown in FIG. 4, the deformable crimping member 46 in the form of a porous sintered disc has an annular outer sidewall 48 and an annular inner sidewall 50, both extending to an upper surface 52 and a lower surface 54. A circular, axial opening 56 is formed in the disc by the inner annular sidewall 50. A radial bore 58 extends from the outer annular sidewall 48 to the inner annular sidewall 50 and the circular opening 56. The radial bore 58 is located approximately an equal distance from the upper and lower surfaces 52, 54 and is sized to receive the electrical contact 30. The electrical contact 30 has a circular cross-section, comprising an annular sidewall 60 extending to an upper face 62 and a lower face 64. An annular groove or channel 66 recessed in the sidewall 60 surrounds the electrical contact and is spaced closer to the lower face 64 than the upper face 62.

Figure 5:
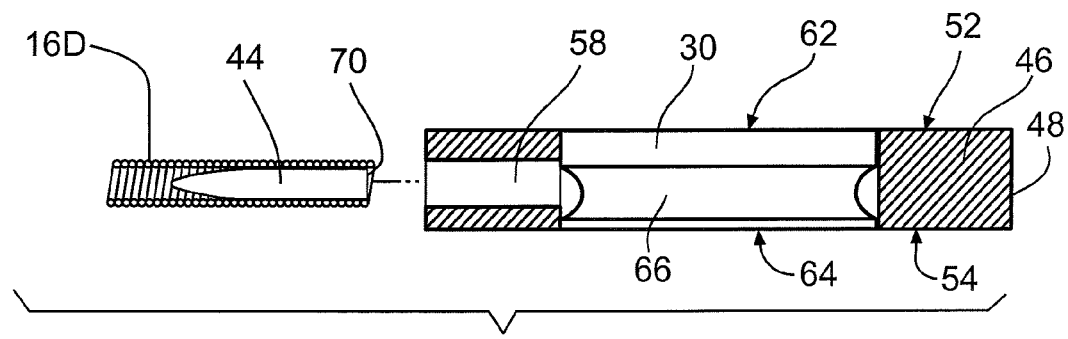
FIG. 5 is a side elevational view, partly in cross-section, of the electrical contact 30 seated in the deformable crimping member 46.

As shown in FIGS. 4 and 5, the electrical contact 30 is received in the circular opening 56 in the deformable crimping member 46 such that the disc sidewall 60 is in a tight-fitting relationship with the inner annular sidewall 50 thereof.

Figure 6:
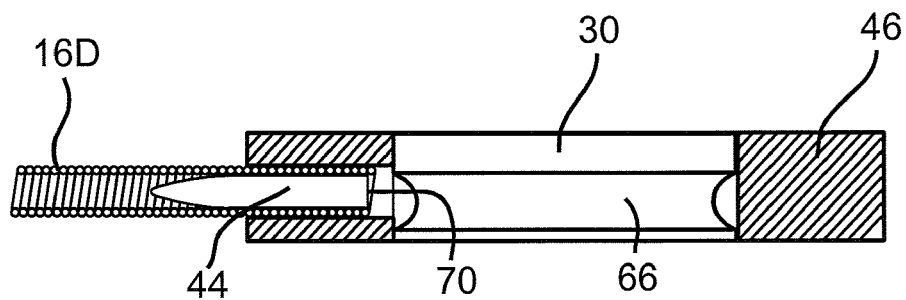
FIG. 6 is a side elevational view, partly in cross-section, of the helical strand 16D/mandrel 44 seated in the deformable crimping member 46.

As shown in FIGS. 4 to 6, the helical strand 16D provides a lumen 68 receiving the tapered mandrel 44 at its distal end. The mandrel 44 has a cylindrically shaped sidewall received in the helical strand lumen in a tight-fitting relationship. Preferably, the mandrel diameter is slightly larger than the inside diameter of the helical strand so it stays in place inside the coil while it is being assembled. A planar distal end 70 of the mandrel 44 is recessed somewhat inside the distal end of the strand 16D. The reason for this is to have the helical strand/mandrel contact interface as great as possible. A proximal end thereof tapers toward the longitudinal axis of the mandrel 44. The taper has a radiused profile with the radius being about 10 to about 20 times the diameter of the mandrel. The helical strand 16D and mandrel 44 received in the lumen 68 thereof is then received in the axial bore 58 of the deformable crimping member 46 with the planar distal mandrel end 70 spaced from the inner disc annular sidewall 50 defining the opening 56. In this position, the longitudinal axis of the mandrel is spaced somewhat toward the upper surface 52 of the deformable crimping member 46 with respect to the center of the annular groove 66.

Figure 7:
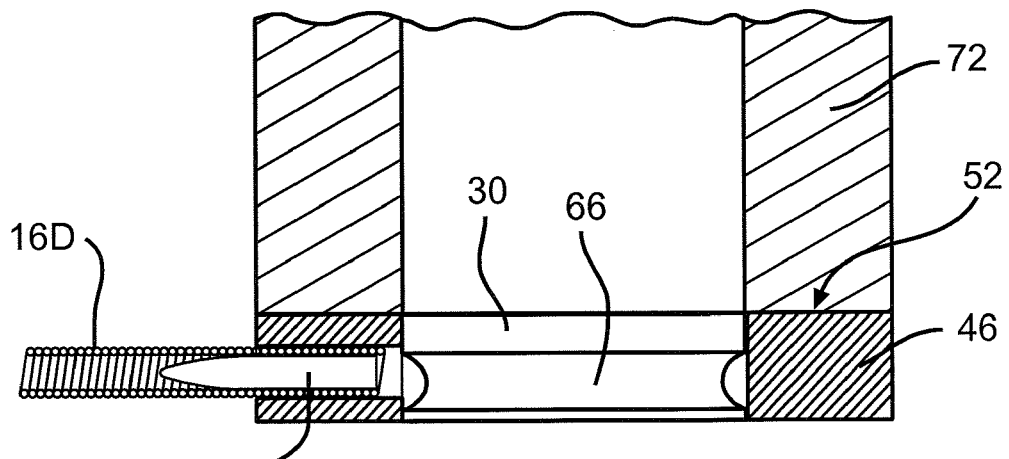
FIG. 7 is a side elevational view, partly in cross-section, showing an annular punching ram 72 prior to deformation of the crimping member 46.
Figure 8:
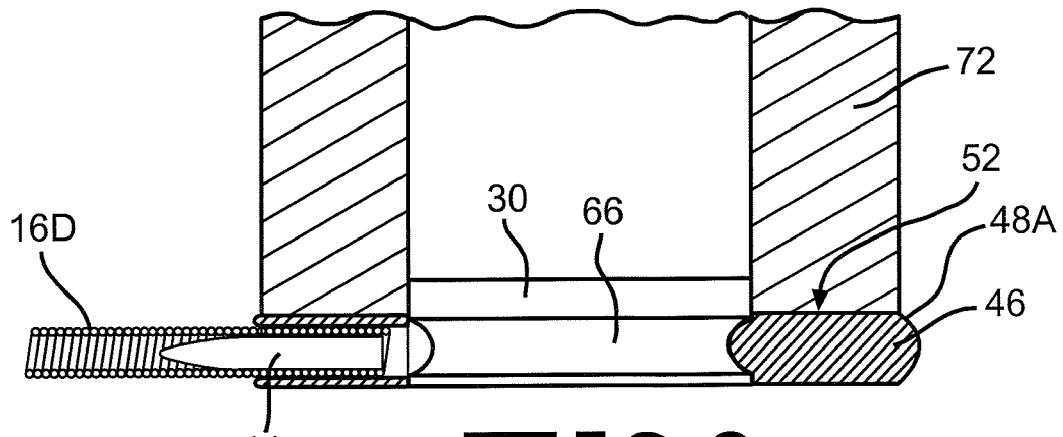
FIG. 8 is a side elevational view, partly in cross-section, showing the crimping member 46 being deformed by the punching ram 72.
Figure 9:
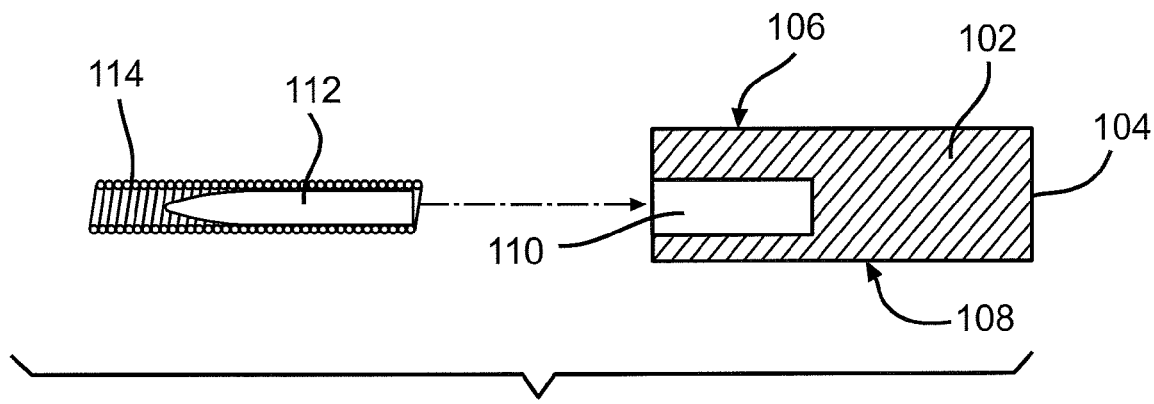
FIG. 9 is a side elevational view, partly in cross-section, of another embodiment of a helical strand 114/mandrel 112 assembly prior to being moved into the axial bore 110 of a deformable electrical contact 102.

As shown in FIG. 7, this assembly is loaded in an open-die punching fixture having an annular ram 72 sized to the exact shape of the upper surface 52 of the deformable crimping member 46 surrounding the electrical contact 30. The porous crimping member is formed by low-pressure pressing or by loose bed sintering of powdered stainless steel, titanium, platinum, or platinum alloy. The powder may be atomized spherical powder particles, or, preferably, "sponge" powder (such as powders reduced from a metal chloride), which have higher strength at the relatively low densities used in the present crimping member. A sintering profile is typically 1,150° C. for three hours at temperature in vacuum for titanium and stainless steel, or 1,625° C. for three hours at temperature in air for platinum to produce a low-density structure combined with a high degree of sintering. The sintered particles have relatively large diameter interparticle necks, but at a relative density of only about 60% to 70%. This allows the porous crimping member to undergo cold coining to a density of around 80% during the crimping process while maintaining its structural integrity.

In that respect, a sufficient amount of force is exerted on the crimping member 46 to compress it into a final shape having its upper surface 52 spaced a relatively short distance from the groove 66. As this occurs, material 46A comprising the crimping member 46 flows by plastic deformation into the groove 66 to lock the deformable disc to the electrical contact 30. This deformation also causes the crimping member 46 to lock onto the rugosity of the helical strand 16D/mandrel 44 assembly. A typical cold coining pressure is about 10,000 psi, which is sufficient to increase the density of the deformable crimping member 46, form the crimp, and intrude the inside diameter material of the crimping member into the electrical contact without pinching off the fine wires of the helical strand 16D.

As shown in the final assembly of FIG. 3, encasing the deformable crimping member 46, helical strand 16 and electrical contact 30 in the biocompatible elastomeric material 32, such as silicone or polyurethane, completes the strip electrode. After cold coining, a longitudinal axis of the mandrel 44 is substantially centered with the trough of the groove 66. After cold coining, the annular outer sidewall of the crimping member assumes the shape of a bulge 48A, which helps lock the polymer material 32 to the crimping member 46. Before deformation, electrical contact 30 is shown having a circular cross section. However, it may also have a frusto-conical shape before deformation to further improve the interlock with the elastomeric material.

Only the upper face of the electrical contact 30 is left exposed. This surface may be impregnated with liquid silicone or other biocompatible resin that is then polymerized to seal the porosity, and to keep body fluids from infusing into the porous electrode and reaching the coiled lead. The remaining surfaces of the electrical contact 30 exposed to the elastomeric material is preferably roughened by grit blasting, machining marks, knurling, and the like to improve adhesion of the potting material to the electrode and stabilize the electrode position.

FIGS. 9 to 12 illustrate another embodiment of a strip electrode 100 according to the present invention. The electrode comprises a porous sintered deformable electrical contact 102 having a surrounding sidewall 104 extending to upper and lower surfaces 106 and 108. Suitable materials for the contact 102 include titanium, zirconium, niobium, molybdenum, palladium, hafnium, tantalum, tungsten, iridium, platinum, gold, and alloys thereof. An annular bore 110 enters the body from the sidewall 104, spaced closer to the lower surface 108 than the upper surface 106.

Figure 10:
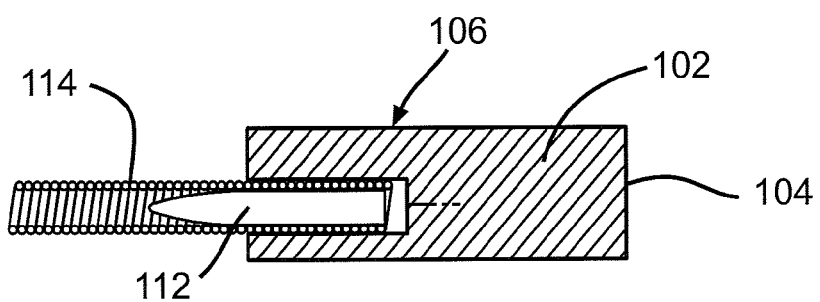
FIG. 10 is a side elevational view, partly in cross-section, showing the helical strand 114/mandrel 112 of FIG. 11 moved into the bore 110 in the deformable electrical contact 102.
Figure 11:
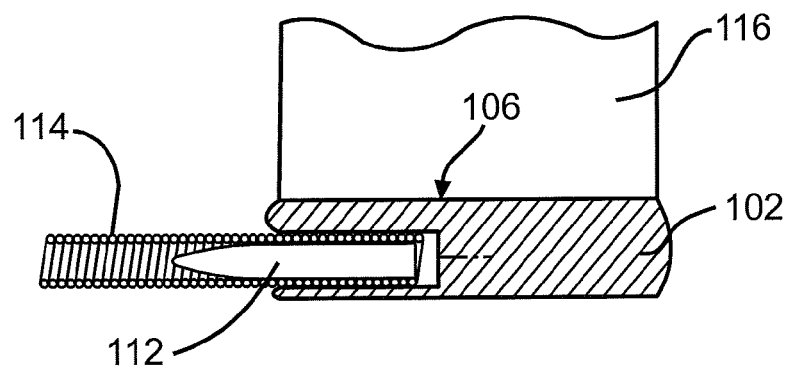
FIG. 11 is a side elevational view, partly in cross-section, showing a punching ram 116 beginning to deform the electrical contact 102.

As shown in FIG. 10, a tapered mandrel 112, similar to the previously described mandrel 44, supported in the lumen at the distal end of a helical strand 114 are received in the bore 110. A pressing ram 116 then deforms the electrical contact 102 into locking contact with the rugosity provided by the coils of the helical strand 114. The electrical contact 102 has a relative density of about 60% to about 70% prior to being deformed under the compression pressure and about 80% after being deformed into the locking relationship.

Encasing the deformed electrical contact 102 and helical strand 114 in a biocompatible elastomeric material 116, such as silicone or polyurethane, completes the electrode 100. After cold coining, the surrounding sidewall of the electrical contact assumes the shape of a bulge 104A. This helps lock the polymer material 116 to the contact. only the upper active surface 106 of the electrical contact 102 is left exposed. In a similar manner as the contact 30 in FIGS. 1 to 8, this upper surface 106 may be impregnated with liquid silicone or other biocompatible resin that is then polymerized to seal the porosity and to keep body fluids from infusing into the porous electrode and reaching the coiled lead.

Figure 12:
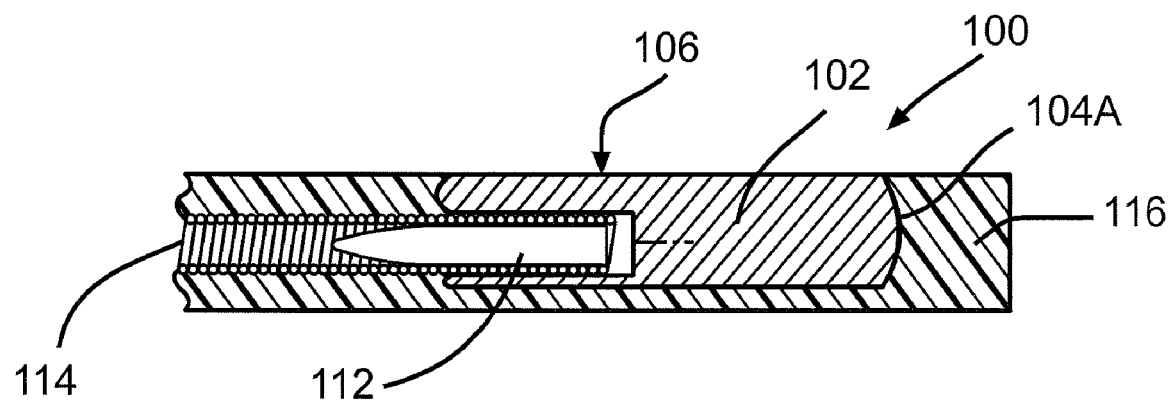
FIG. 12 is a side elevational view, partly in cross-section, showing the helical strand 114 crimped to the electrical contact 102 and encased in an elastomeric material 116.
Figure 13:
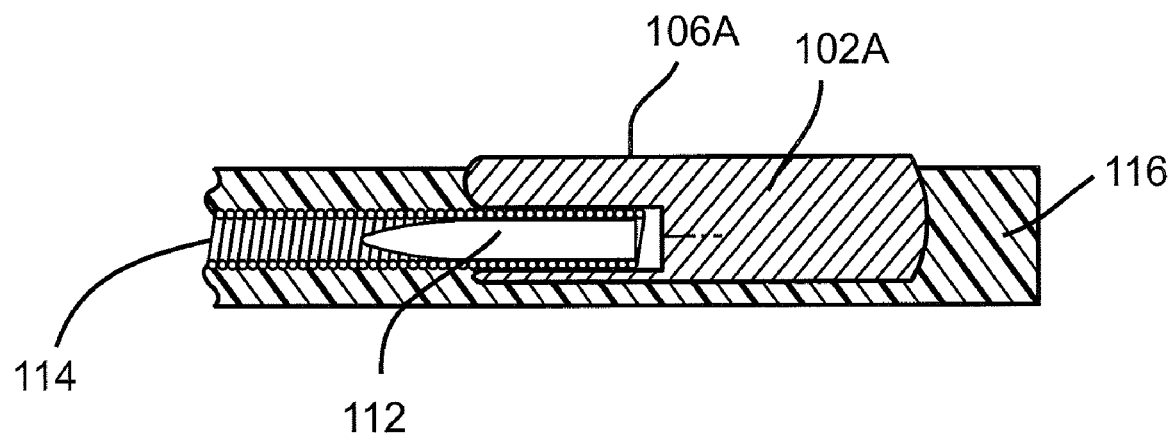
FIG. 13 illustrates another embodiment of an electrical contact 102A having its upper surface 106A spaced above the elastomeric material 116.

In FIG. 12, the upper surface 106 of the electrical contact 102 is substantially coplanar with that of the elastomeric material 116. In FIG. 13, the upper surface 106A of the electrical contact 102A is spaced above the upper surface of the elastomeric material.

An important aspect of the present embodiments illustrated in FIGS. 1 to 12 is that the extended, tapered mandrels 44, 112 distribute the bending, flexing and twisting strain forces caused by body movement over a greater length of the helical strands 16D, 114 than in a mandrel having a blunt end. This is shown in FIG. 15 by the gap of arrows designated 118 in comparison to the strain distribution indicated by the gap of arrows 120 afforded by a mandrel 122 having a blunt end construction according to the prior art as shown in FIG. 14.

The length of gap 118 is about 1 to 5 diameters of the helical strand, preferably about 2 to 3 diameters. In the blunt end mandrel 122, strain forces on the helical strand 124 moving along a 20° arc are significantly more concentrated in comparison to a similar degree of movement in the present construction.

Another embodiment of a strip electrode 130 comprising an electrical contact 132 secured to a helical strand 134 according to the present invention is shown in FIG. 16.

Machining, stamping, metal injection molding, drawing, and any other suitable method can make the contact 132. In the case of machining and metal injection molding, the mandrel/contact assembly may also be formed as a single integral unit. This electrode comprises a mandrel 136 having a tapered nose 138 received in the lumen of the helical strand 134. A significant portion of the mandrel 136 extends out the distal end of the helical strand 134. A distal end of the mandrel 136 is in the shape of a spherical ball 140 sized about 0.010 inches larger in diameter than that of the mandrel. The distal ball 140 is secured to the back face 142 of the electrical contact 132 by braze, weldment, or solder joint 144. An effective braze load is about 10 mg of gold at a temperature of about 1,100° C. for two seconds at temperature. Many other braze materials other than gold can be used, however, for example gold—tin or copper—silver braze alloys.

An annular or semi-annular socket 146 is positioned on the distal end of the helical strand 134 with the mandrel received in the lumen thereof. The crimp is accomplished by radial deformation of the socket 146. That way, the material of the socket 146 plastically deforms into the rugosity of the helical strand 134 that, in turn, tightly surrounds the cylindrical intermediate section of the mandrel 136. Materials appropriate for the socket 146 include stainless steel, titanium, niobium, zirconium, platinum and platinum alloys, and other biocompatible deformable materials. The entire assembly is encased in a elastomeric material 148 such as silicone or polyurethane with only the active surface 150 of the electrical contact 132 being left exposed. This construction provides improved isolation of the crimp joint from body fluids that may diffuse along the electrical contact/elastomer interface.

FIG. 17 illustrates a further embodiment of a strip electrode 150 comprising an electrical contact 152 secured to a helical strand 154 according to the present invention. A mandrel 156 has its distal end received in an axial opening 158 in the contact 152. A braze, weldment or solder joint 160 secures the mandrel to the contact. Then, the mandrel 156 is bent until the longitudinal axis of the helical strand 154 is substantially parallel to the upper contact face 162.

Connection of the mandrel 156 to the helical strand 154 is similar to that shown in FIG. 16 with a deformable socket 164 clamped onto the helical strand receiving the mandrel. Finally, the entire assembly is encased in an elastomeric material 166, such as silicone or polyurethane, with only the active contact face 162 left exposed.

Figure 18:
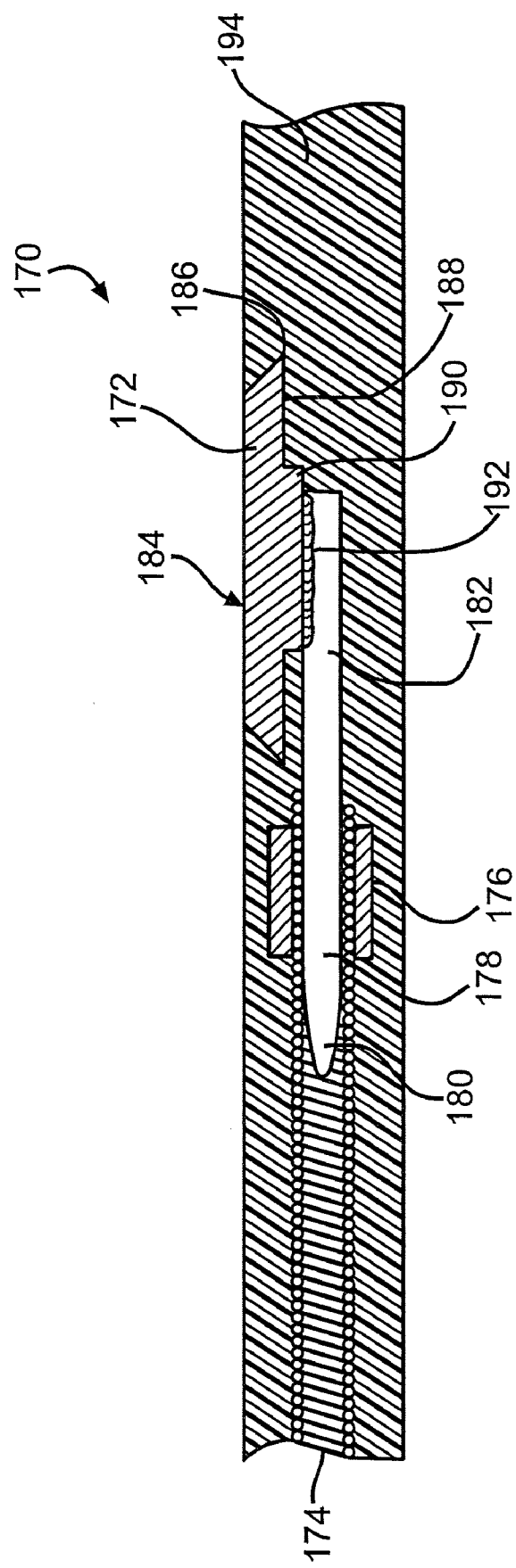
FIG. 18 is a side elevational view, partly in cross-section, of another embodiment of a mandrel 178 crimped to a helical strand 174 secured to the land 190 of an electrical contact 172 and encased in an elastomeric material 194.

FIG. 18 illustrates a further embodiment of a strip electrode 170 comprising an electrical contact 172 secured to a helical strand 174 by a deformable crimp socket 176 according to the present invention. A cylindrically shaped mandrel 178 having a tapered nose 180 is received in the lumen of the helical strand 174. A distal portion 182 of the mandrel 178 extends out the distal end of the helical strand 174. The electrical contact 172 comprises a contact face 184 extending downwardly and outwardly to form a chamfered edge 186. The back face 188 has a protruding land 190 to which the distal portion 182 of the mandrel is secured by braze, weldment or solder joint 192. To further enhance this connection, the distal portion 182 of the mandrel may have a flat surface received in a coinciding groove or channel in the land 190. This assembly is then encased in an elastomeric material 194, such as silicone or polyurethane, with only the contact face 184 left exposed.

Figure 19:
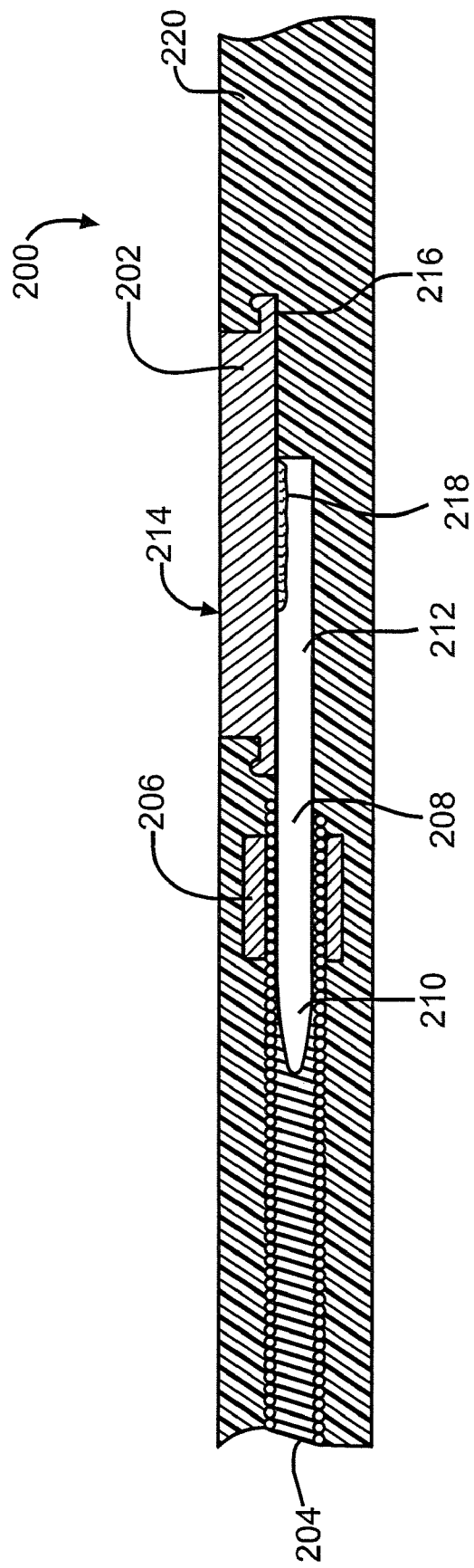
FIG. 19 is a side elevational view, partly in cross-section, of another embodiment of a mandrel 208 crimped to a helical strand 204 secured to an electrical contact 202 provided with a flange 216 and encased in an elastomeric material 220.

FIG. 19 illustrates a further embodiment of a strip electrode 200 comprising an electrical contact 202 secured to a helical strand 204 by a deformable crimp socket 206 according to the present invention. A mandrel 208 having a tapered nose 210 is received in the lumen of the helical strand 204. A distal portion 212 of the mandrel 208 extends out the distal end of the helical strand 204. The electrical contact 202 comprises a contact face 214 extending downwardly to a flange 216. As with the strip electrode 170 of FIG. 18, the distal portion 212 of the mandrel is cylindrical, flattened or of some other cross-section, received in a coinciding groove or channel on the back face 216 of the contact 202 secured thereto by a braze, weldment or solder joint 218. This assembly is then encased in a elastomeric material 220 with only the contact face 214 left exposed.

Figure 20:
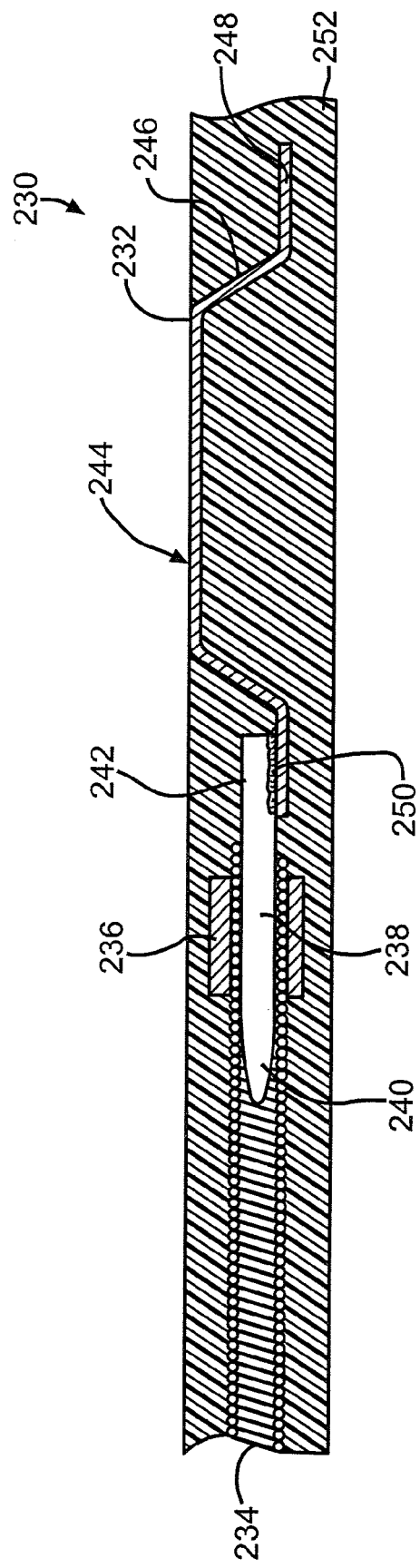
FIG. 20 is a side elevational view, partly in cross-section, of another embodiment of a mandrel 238 crimped to a helical strand 234 secured to a deep drawn electrical contact 232 and encased in an elastomeric material 252.

FIG. 20 illustrates a further embodiment of a strip electrode 230 comprising a deep drawn electrical contact 232 secured to a helical strand 234 by a deformable crimp socket 236 according to the present invention. A mandrel 238 having a tapered nose 240 is received in the lumen of the helical strand 234. A distal portion 242 of the mandrel 238 extends out the helical strand 234. The electrical contact 232 is made of a conductive metal such as any one previously described as useful for the contacts shown in alternate embodiments of the present invention. The electrical contact 232 has an upper contact face 244 connected to a frusto-conical portion 246 extending downwardly and outwardly to a surrounding rim 248. The rim 248 is generally parallel to the plane of the contact face 244. The distal portion 242 of the mandrel is secured to the rim 248 by braze, weldment or solder joint 250. Preferably, the distal portion of the mandrel 238 and that portion of the rim 248 supporting the mandrel have coinciding shapes for added strength to the connection. This assembly is then encased in an elastomeric material 252 with only the contact face 244 left exposed.

Thus, the present invention has been described with respect to various structures and methods for making high reliability electrical attachments between coiled leads and flat electrodes such as strip electrodes found in implantable neurostimulator systems. The attachment requirements of biocompatibility, isolation from body fluids, and long-term mechanical/electrical continuity under cyclic stress are met by the novel mandrel received in the helical strand connected to the electrical contact by the deformable crimping member, the deformable contact itself, or by the mandrel being secured to the contact through a braze, weldment or solder joint.

It is appreciated that various modifications to the inventive concepts described herein may be apparent to those of ordinary skill in the art without departing from the spirit and scope of the present invention as defined by the appended claims.

What is claimed is:

1. An electrode for an implantable medical device, the electrode comprising:
   a) an electrical contact having an electrical contact sidewall extending from an electrical contact upper face to an electrical contact lower face, wherein the electrical contact has a radial bore extending from the electrical contact sidewall part way across a diameter thereof between its upper and lower faces;
   b) at least one electrical conductor extending from a proximal end connectable to the medical device to a distal portion having a helical shape forming a lumen;
   c) a mandrel comprising a sidewall extending along a longitudinal axis thereof from a distal mandrel portion to a proximal mandrel portion comprising a tapered nose that extends downwardly and inwardly along the longitudinal axis to a proximal end thereof, wherein the mandrel is received in the lumen at the distal portion of the at least one electrical conductor received in the bore of the electrical contact and wherein the tapered nose of the proximal mandrel portion is received in the lumen of the at least one electrical conductor, but not in the bore of the electrical contact.

2. The electrode of claim 1 wherein the mandrel has a cylindrical sidewall extending along the longitudinal axis thereof to the tapered nose.

3. The electrode of claim 1 wherein the distal mandrel portion received in the distal portion of the at least one electrical conductor received in the bore of the electrical contact is brazed, welded or soldered thereto.

4. The electrode of claim 1 wherein the electrical contact is a deep drawn member.

5. The electrode of claim 1 wherein the tapered nose of the mandrel has a length that is from about 1 to 5 times the diameter of the coil of the coiled filar.

6. The electrode of claim 1 wherein the tapered nose of the mandrel has a radiused profile with the radius being about 10 to about 20 times the diameter of the mandrel.

7. The electrode of claim 1 wherein the upper face of the electrical contact is planar.

8. The electrode of claim 1 wherein an elastomeric material encases at least the distal portion of the at least one electrical conductor and at least the sidewall of the electrical contact, but with the upper face thereof remaining exposed.

9. An electrode for an implantable medical device, the electrode comprising:
   a) an electrical contact having a sidewall extending to an upper face and a lower face, wherein a radial bore is provided in the electrical contact sidewall part way across a diameter thereof;
   b) at least one electrical conductor comprising a proximal end connectable to the medical device and a distal portion comprising at least one coiled filar providing a rugosity;
   c) a mandrel comprising a cylindrical sidewall extending along a longitudinal axis thereof from a distal mandrel portion to a proximal mandrel portion comprising a tapered nose extending downwardly and inwardly along the longitudinal axis to a proximal end thereof, wherein the mandrel is received in a lumen at the distal portion of the coiled filar and wherein at least a portion of the coiled filar supporting the distal mandrel portion is movable into the bore of the electrical contact which is then deformable under a compression pressure to lock onto the rugosity of the coiled filar with the distal mandrel portion preventing damage to the coiled filar; and
   d) an elastomeric material encasing at least the distal portion of the coiled filar and at least a portion of the electrical contact, but with the upper face thereof remaining exposed.

10. The electrode of claim 9 wherein the elastomeric material encases only a portion of the sidewall of the electrical contact, spaced below the upper face thereof.

11. The electrode of claim 9 wherein the elastomeric material encases the entire sidewall of the electrical contact.

12. The electrode of claim 9 wherein the longitudinal axis of the mandrel is spaced closer to the lower face than the upper face.

13. The electrode of claim 9 wherein the tapered nose of the mandrel has a length that is from about 1 to 5 times the diameter of the coil of the coiled filar.

14. The electrode of claim 9 wherein the tapered nose of the mandrel has a radiused profile with the radius being about 10 to about 20 times the diameter of the mandrel.

15. The electrode of claim 9 wherein the electrical, contact has a relative density of about 60% to about 70% prior to being deformed under the compression pressure and about 80% after being deformed into the locking relationship with the coiled filar.

16. A method for providing an electrode for an implantable medical device, comprising the steps of:
   a) providing an electrical contact comprising an electrical contact sidewall extending from an electrical contact upper face to an electrical contact lower face, wherein the electrical contact has a radial bore extending from the electrical contact sidewall part way across a diameter thereof between its upper and lower faces;
   b) providing at least one electrical conductor extending from a proximal end connectable to the medical device to a distal portion having a helical shape forming a lumen;
   c) providing a mandrel comprising a sidewall extending along a longitudinal axis from a distal mandrel portion to a proximal mandrel portion comprising a tapered nose extending downwardly and inwardly along the longitudinal axis to a proximal end thereof;
   d) positioning the mandrel in the lumen at the distal portion of the at least one electrical conductor; and
   e) positioning the distal mandrel portion received in the lumen at the distal portion of the at least one electrical conductor in the bore of the electrical contact with the tapered nose at the proximal mandrel end received in the lumen of the at least one electrical conductor, but not in the bore of the electrical contact.

17. The method of claim 16 including encasing at least the distal end of the helical strand and at least a portion of the electrical contact in an elastomeric material with the upper face of the electrical contact remaining exposed.

18. An electrode for an implantable medical device, the electrode comprising:
   a) an electrical contact having an electrical contact sidewall extending from an electrical contact upper face to an electrical contact lower face, wherein the electrical contact has a radial bore extending from the electrical contact sidewall part way into a depth thereof between its upper and lower faces;
   b) at least one electrical conductor extending from a proximal end connectable to the medical device to a distal portion having a helical shape forming a lumen;
   c) a mandrel comprising a sidewall extending along a longitudinal axis thereof from a distal mandrel portion to a proximal mandrel portion, wherein the mandrel is received in the lumen at the distal portion of the at least one electrical conductor received in the radial bore of the electrical contact and wherein the proximal mandrel portion is received in the lumen of the at least one electrical conductor, but not in the bore of the electrical contact.

19. The electrode of claim 18 wherein the radial bore extends from the electrical contact sidewall part way across a diameter of the electrical contact.

20. An electrode for an implantable medical device, the electrode comprising:
   a) an electrical contact having a sidewall extending to an upper face and a lower face, wherein a radial bore is provided in the electrical contact sidewall;
   b) at least one electrical conductor comprising a proximal end connectable to the medical device and a distal portion comprising at least one coiled filar providing a rugosity;
   c) a mandrel comprising a cylindrical sidewall extending along a longitudinal axis thereof from a distal mandrel portion to a proximal mandrel portion, wherein the mandrel is received in a lumen at the distal portion of the coiled filar and wherein at least a portion of the coiled filar supporting the mandrel is movable into the bore of the electrical contact which is then deformable under a compression pressure to lock onto the rugosity of the coiled filar with the distal mandrel portion preventing damage to the coiled filar and with the proximal mandrel portion received in the lumen of the at least one electrical conductor, but not in the bore of the electrical contact; and d) an elastomeric material encasing at least the distal portion of the coiled filar and at least a portion of the electrical contact, but with the upper face thereof remaining exposed.

21. The electrode of claim 20 wherein the radial bore extends from the electrical contact sidewall part way across a diameter of the electrical contact.

* * * * *